United States Patent
Bauer et al.

(10) Patent No.: US 6,630,018 B2
(45) Date of Patent: *Oct. 7, 2003

(54) COLORED AND COATED PLATELETLIKE PIGMENTS

(75) Inventors: Gerd Bauer, Kleinostheim (DE); Karl Osterried, Dieburg (DE); Christoph Schmidt, Kelkheim (DE); Reiner Vogt, Pfungstadt (DE); Helge-Bettina Kniess, Weiterstadt (DE); Michael Uhlig, Weiterstadt (DE); Norbert Schül, Heppenheim (DE); Günther Brenner, Griesheim (DE)

(73) Assignee: Merck Patent Gesellschaft mit beschränkter Haftung, Darmstadt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/211,791
(22) PCT Filed: Oct. 12, 1992
(86) PCT No.: PCT/EP92/02351
§ 371 (c)(1), (2), (4) Date: Apr. 15, 1994
(87) PCT Pub. No.: WO93/08237
PCT Pub. Date: Apr. 29, 1993

(65) Prior Publication Data
US 2003/0047115 A1 Mar. 13, 2003

(30) Foreign Application Priority Data
Oct. 18, 1991 (DE) .......................... 41 34 600
Nov. 22, 1991 (DE) .......................... 41 38 376
Apr. 10, 1992 (DE) .......................... 42 12 119
May 9, 1992 (DE) .......................... 42 15 276

(51) Int. Cl.$^7$ .............................................. C09C 1/00
(52) U.S. Cl. ................. 106/415; 106/418; 106/417; 106/472; 106/482; 106/483; 106/459; 106/450; 106/453
(58) Field of Search ............................ 106/417, 442, 106/418, 415, 472, 482, 483, 459, 450, 453; 428/403, 404

(56) References Cited

U.S. PATENT DOCUMENTS

| | | | |
|---|---|---|---|
| 3,138,475 A | | 6/1964 | Schröder et al. |
| 3,627,553 A | | 12/1971 | Clark et al. |
| 3,767,443 A | | 10/1973 | Clark et al. |
| 3,884,835 A | * | 5/1975 | Vaughan ...................... 106/415 |
| 4,435,220 A | * | 3/1984 | Watanabe et al. ........... 106/418 |
| 4,867,793 A | * | 9/1989 | Franz et al. ................. 106/415 |
| 4,882,133 A | * | 11/1989 | Saegusa |
| 5,074,917 A | | 12/1991 | Persello |
| 5,106,419 A | * | 4/1992 | Hechler et al. .............. 106/418 |

(List continued on next page.)

FOREIGN PATENT DOCUMENTS

| | | | |
|---|---|---|---|
| FR | 1273230 | | 8/1961 |
| JP | 62-270409 | * | 11/1987 |

*Primary Examiner*—C. Melissa Koslow
(74) *Attorney, Agent, or Firm*—Millen, White, Zelano & Branigan, P.C.

(57) ABSTRACT

The invention relates to a platelet-shaped pigment having high luster and high covering power or high transparency, consisting of a transparent, inorganic, platelet-shaped matrix which can contain an additional constituent, characterized in that the additional constituent is a soluble or insoluble colorant and in that the matrix is coated at least on one side with one or more thin, transparent or semi-transparent reflective layers of metal oxides or metals to achieve the luster.

17 Claims, 3 Drawing Sheets

U.S. PATENT DOCUMENTS

| | | | |
|---|---|---|---|
| 5,127,952 A | * | 7/1992 | Persello et al. .............. 106/442 |
| 5,238,492 A | * | 8/1993 | Itoh et al. |
| 5,271,770 A | * | 12/1993 | Noguchi et al. ............ 106/417 |
| 5,326,633 A | * | 7/1994 | Clough et al. |
| 5,340,393 A | * | 8/1994 | Jacobson .................... 106/442 |
| 6,267,810 B1 | * | 7/2001 | Pfaff et al. ................... 106/415 |
| 6,270,563 B1 | * | 8/2001 | Herget et al. ................ 106/415 |
| 6,294,010 B1 | * | 9/2001 | Pfaff et al. ................... 106/415 |
| 6,334,893 B1 | * | 1/2002 | Pfaff et al. ................... 106/442 |
| 6,372,036 B1 | * | 4/2002 | Pfaff et al. ................... 106/443 |
| 6,432,195 B1 | * | 8/2002 | Rathschlag et al. ......... 106/500 |

* cited by examiner

COLORED AND COATED PLATELETLIKE PIGMENTS

The invention relates to platelet-shaped pigments having high luster and high covering power or high transparency.

Covering power and luster can, in the case of platelet-shape pigments, often be achieved simultaneously to a satisfactory degree only with difficulty. Thus, mica platelets which are coated, for example, with one or more ma thin metal oxide layers are distinguished by interference colors and high luster, but at the same time also, as a result of the transparent substrate, by a high transparency and thus a comparatively low covering power. It is true that the covering power can be improved by using colored metal oxide layers composed, for example, of chromium oxide or iron oxide, but even the covering power of pigments of this type often do not meet all requirements. The covering power can be further increased if a rough substrate surface is present or if relatively rough metal oxide layers are deposited. The increased number of scattering centers increases the covering power but decreases the luster.

Depending on the refractive index of the metal oxide used and on the desired interference color, the thickness of the metal oxide layers is typically between 50 and 250 nm. Since reflections occur at the phase boundary of materials having different optical refractive indices, interference effects which depend on the angle of observation and the optical densities of the metal oxide layers are observed on parallel alignment of the platelet-like pigments in the reflected light; the corresponding complementary colour is seen in the transmitted light with non-absorbing materials.

A condition for the occurrence of interference effects of this type is a smooth substrate surface.

Until now, natural materials such as, for example, mica have mainly been used as platelet-shaped substrates for the production of interference pigments. Since this is a naturally occurring material, the surface of substrates of this type is not ideally smooth, but has irregularities such as, for example, steps, as a result of which the quality of the resulting interference pigments is limited.

A further disadvantage of natural materials, such as, for example, mica, is contamination by coloring foreign ions, for example iron ions, which have an adverse effect on the color purity of the final product.

Furthermore, it has been proposed to use platelet-shaped metal substrates instead of transparent mica, which leads to pigments having very high covering power. On the other hand, this simultaneously results in a very hard, metallic luster, which is often aesthetically not completely satisfactory. In addition, metal pigments do not have a deep action since the incident light is immediately reflected by the surface.

Thin glass sheets obtained by rolling a glass melt followed by milling have been proposed as the synthetic material. It is true that interference pigments based on such materials show color effects which are superior to conventional mica-based pigments. However, their disadvantage is that the glass sheets have a very high average thickness of about 10–15 $\mu$m and a very broad distribution of thicknesses (typically of between 4 and 20 $\mu$m), while the thickness of interference pigments is typically not more than 3 $\mu$m. EP 0,384,596 describes a process in which hydrated alkali metal silicate is treated with a jet of air at temperatures of 480–500° C., resulting in the formation of bubbles having small wall thicknesses; the bubbles are then comminuted, giving platelet-shaped alkali metal silicate substrates having a thickness of less than 3 $\mu$m. However, the process is complicated and the distribution of thicknesses of the platelets obtained is relatively broad.

EP 0,240,952 proposed a continuous belt process for the preparation of various platelet-shaped materials, also including silica. In this process, a thin liquid film of defined thickness of a precursor of the platelet-like material is applied to a smooth belt via a system of rollers; the film is dried and peeled off from the belt, thus forming platelet-shaped particles. The particles are then, if desired, ignited and, if desired, milled, followed by classification.

Precursor materials used are organometallic: compounds (alkoxides), such as, for example, tetraethyl orthosilicate. The film is polymerized by drying and is scraped off the belt using a scraper, small platelets being obtained; these are then ignited at temperatures of 500° C. to convert them into the corresponding metal oxide. A metal oxide sol which is optionally dispersed in methanol and which is applied as a film, dried and ignited in an analogous manner is additionally used as a precursor.

However, a disadvantage is the use of very expensive precursor materials and in particular the increased requirements of workplace safety which are necessary when organometallic compounds are used. In order to achieve complete chemical conversion of the precursor into the desired film material, vigorous heating of the film and of the belt material are usually necessary. Apart from the resulting substantial thermal stress on the belt material, the high amount of energy used and the limitation of the process rate also have a very disadvantageous effect on the economy of the process.

The use of aqueous oxide or hydroxide sols described in EP 0,236,952 is also problematical, since the films formed are not homogeneous but are composed of irregularly sized particles. This requires a treatment at very high temperatures in order to give the material the necessary homogeneity, precision of shape and strength.

U.S. Pat. No. 3,138,475 describes a continuous belt process for the preparation of platelet- or leaf-shaped oxides or hydrated oxides of metals from groups IV and V and the iron group of the periodic table. In this process, first, if desired, a release layer comprising, for example, a silicone coating, is applied to a continuous belt in order to facilitate the later peeling-off of the metal oxide film. A liquid film comprising a solution of a hydrolyzable compound of the metal to be converted into the desired oxide is then applied, the film is dried and then peeled off by means of a shaking device. It is true that this publication mentions that it is also possible to prepare $SiO_2$ platelets by this process, but the process is described only very generally and no concrete example is given.

JP 64-9803 describes a process for the preparation of a platelet-shaped metal oxide containing dispersed fine particles of a second metal oxide of higher refractive index on a continuous belt. The products obtained by this process, which are used as light protection filters in cosmetics, consist, for example, of a matrix of silica in which fine particles of titanium dioxide are dispersed. However, this product shows no interference colors, since the titanium dioxide particles acting as scattering centers are not uniformly distributed on a smooth surface.

JP 2-32,170 discloses a pigment which consists of a base material, for example a titanium dioxide-mica pigment, in which colloidal metal particles (silver) are sputtered onto a first interference layer of titanium dioxide. As a second interference layer, titanium dioxide is then in turn applied as a covering layer. This pigment has the disadvantage that white cannot be produced, since the metal particles absorb and thus give the product a dark color. In addition, production is very expensive, since four different layers have to be applied using different processes.

A pigment of similar construction is disclosed in EP-A-0,484,108. Titanium is applied by sputtering to a titanium dioxide-mica pigment as base material. A part of the titanium reduces the titanium dioxide of the base material to suboxides, which act as light-absorbing regions on the pigment surface. The remaining unchanged titanium particles impart metallic lustre to the pigment.

Apart from the high production costs, only dark pigments of low transparency can be prepared by this process. In addition, interference colors cannot be produced.

The object of the present invention is to make available platelet-shaped interference pigments having a high gloss and high covering power or high transparency, which can be prepared using a simple and economical process.

This object is achieved according to the present invention by the provision of a platelet-shaped pigment having high luster and high covering power or high transparency, consisting of a transparent, inorganic, platelet-shaped matrix which can contain an additional constituent, the additional constituent being a soluble or insoluble colorant and being coated at least on one side with one or more thin, transparent or semi-transparent reflective layers of metal oxides or metals to achieve the luster.

Furthermore, this object of the invention is achieved by a process for the preparation of the pigments according to the invention, which consists of a transparent, inorganic, platelet-shaped matrix which can contain an additional constituent and which is coated with one or more thin, transparent or semi-transparent reflective layers of metal oxides or metals, in which a precursor of the matrix material is applied to a continuous belt as a thin film, the liquid film is solidified by drying, in the solidified film, the matrix is produced from the precursor by means of a chemical reaction, the resulting layer is then separated from the support medium and washed and the particles are optionally dried, ignited, ground and classified, which is characterized in that the film solidified by drying is then treated with an acid and the film particles obtained are coated with one or more reflective layers of metal oxides or metals.

Expedient embodiments are given in the sub-claims.

The invention additionally relates to the use of the pigments prepared according to the invention in formulations such as paints, printing inks, cosmetics or plastics or as anti-corrosion agents.

The pigments according to the invention are based on a platelet-shaped, transparent matrix which can be modified by network-forming agents or network modifiers, such as, for example, aluminum oxide, boron oxide or phosphorus oxide, sodium oxide, lithium oxide, potassium oxide or calcium oxide. The matrix can consist, for example, of silicon dioxide, silicates, boron oxide, borates, aluminium oxide, aluminates or other materials which are transparent, stable and capable of absorbing soluble or insoluble colorants. The platelet-shaped matrix particles typically have a thickness between 0.05 and 5 $\mu$m and in particular between 0.2 and 2.0 $\mu$m. The size in the two other dimensions is customarily between 1 and 250 $\mu$m and in particular between 2 and 100 $\mu$m.

Starting materials (precursors) employed for the preparation of the matrix are solutions of inorganic or organic compounds of the metals aluminum, silicon, potassium or sodium with, for example, borates, aluminates, poly- or metaphosphates, silicates or mixtures thereof. A preferred precursor is sodium silicate.

Pigment particles whose dimensions are distinctly smaller than those of the matrix are incorporated, in general in an irregular three-dimensional manner, in the matrix as insoluble colorants. These are spherical or three-dimensional irregularly formed particles having a maximum size of less than 3 $\mu$m and in particular of less than 1 $\mu$m, even smaller pigments being frequently preferred. Agglomerates of commercially available pigments, which can have too great a size, are preferably comminuted in a ball mill, in a sand mill or in a similar device. However, larger pigment particles can also sometimes be used, where, however, the average size of the pigment particles in each case should be smaller than the average thickness of the matrix in order to enable the formation of smooth, thin, luster-producing layers. The term pigment particle is to be understood here in a broad sense and includes white, black, colored and luminous pigments.

Examples of suitable inorganic pigment particles are white pigments, such as, for example, titanium dioxide, barium sulfate or zinc oxide, black pigments, such as, for example, magnetite or pigment black and also colored pigments, such as, for example, iron oxide or chromium oxide, mixed-phase oxides, such as, for example, (Ti, Cr, Sb)$O_2$, $CoAl_2$, $O_4$ (Thenard's Blue), $ZnAl_2O_4$ (Rinman's Green), (Fe, Cr)$_2O_3$, furthermore sulfides, such as, for example, CdS and other inorganic colored pigments. Inorganic luminous pigments, such as, for example, fluorescent silver-doped zinc oxide or phosphorescent copper-doped zinc sulfide or ultramarine pigments are also suitable.

Suitable organic pigments are azo pigments, anthraquinone pigments, indigo or thioindigo derivatives, diketopyrrolopyrrole pigments, perylene pigments or phthalocyanine pigments.

The pigment particles listed here as well as the processes for their preparation are known (see, for example, R. Kittel, Wissenschaftliche Verlagsgesellschaft, Stuttgart 1960, G. Benzig, Pigmente für Anstrichmittel, Expert Verlag 1988) and they are usually also commercially available. However, these pigment particles are only to be understood as examples and they are solely intended to illustrate the invention without limiting it in any way. Apart from the pigment particles mentioned explicitly, a large number of further pigment particles can be used.

In many cases, it is advantageous, for better dispersion of the pigment particles in the precursor solution, to add wetting agents, for example nonionic and/or ionic commercially available grades. Thus, for example, polyethylene glycols and polypropylene glycols are very suitable. Neither the type nor the amount of the wetting agent added is critical, although in general the maximum amount of wetting agent is 2% by weight, relative to the dispersion.

As an additional constituent, the matrix can also contain a soluble colorant. The term "soluble colorant" is either to be understood as meaning a color-imparting metal oxide or a soluble organic dye. These soluble colorants can be present in the inorganic matrix either as the sole constituent or together with an insoluble colorant, i.e. with a pigment.

The soluble organic dye is, for example, a hydroxyanthraquinone dye which is soluble in alkali or an acidic azo dye.

To prevent possible "bleeding-out" of the soluble colorant from the matrix during coating with a metal oxide, an $SiO_2$ layer can additionally be applied to the matrix.

The colour-imparting metal oxide is, for example, iron oxide, chromium oxide or cobalt oxide. Color-imparting compounds which are generally suitable for coloring the matrix are those of the metals titanium, vanadium, chromium, manganese, iron, cobalt, nickel and copper, preferably compounds of cobalt, copper, iron and chromium. They are added to the precursor of the matrix material as soluble compounds.

A colored, transparent pigment having a colour scale similar to that of colored, transparent glass is obtained. By adding iron compounds, for example, red-brown shades are obtained, by adding chromium compounds green shades and by adding cobalt compounds blue shades.

The pigment has a particularly high transparency, since as a result of the smooth surface of the platelets and the lack of light-scattering particles in the matrix virtually no light is scattered.

The lustre of the matrix particles already present due to the smooth surface is enhanced by the application of reflective layers, for example of metal oxides. Interference colors are thus simultaneously produced.

Due to the combination of luster effect and absorption color, brilliant colour impressions, for example for automobile finishes or for the coloring of plastics, can be achieved.

The colored matrix particles can also be employed in various formulations without additional coating.

The soluble or insoluble colorant is present in the uncoated substrate in a proportion of 0.01% by weight to 50% by weight, preferably 1% by weight to 30% by weight.

It has been found that by addition of barium sulfate to the matrix a smoothing of the surface of the platelet-shaped matrix particles takes place. During subsequent coating with metals or metal oxides, thereby a higher luster of the pigment is thereby achieved.

Barium sulfate having a particle size of 20 nm to 500 nm, preferably 100 nm to 300 nm, is dispersed in the precursor of the matrix material. Commercially available products, for example BF 10 from Nordmann, Rassman GmbH & Co. can be employed.

The proportion of barium sulfate in uncoated substrate is 1% by weight to 50% by weight, preferably. 10% by weight to 25% by weight.

The platelet-shaped matrix particles which contain an insoluble and/or soluble colorant are coated with one or more thin, transparent or semi-transparent, reflective layers of metal or metal oxides which serve to produce the luster. Preferred reflective metal layers consist of silver, gold, palladium, platinum, aluminum, chromium or copper.

According to the invention, pigments whose matrix is coated on at least one side with a thin, semi-permeable metal layer are preferred. The metal layer typically has a thickness of between 5 and 25 nm and in particular between 5 and 15 nm and is composed, for example, of Al, Cr, Ag, Au, Cu or else other metals. The metal layer is very smooth and reflects-depending on its thickness—a larger or smaller proportion of the incident light. The remaining light enters the matrix and, if the particles are absorption pigment particles, some of it is absorbed and some is scattered by the incorporated pigment particles, and the remaining light passes through. If the pigments according to the invention have been applied to a surface, for example as part of a paint formulation, they align themselves, due to their platelet-shaped structure, more or less parallel with respect to one another in successive layers on top of each other, and the light, transmitted through pigments at a higher level is, as described above reflected, absorbed, scattered and transmitted by pigments of the levels below. The overall effect of the above-described special embodiment of the pigments according to the invention is thus high luster, variable in a wide range, in combination with the color of the incorporated pigments and a high covering power, which is due to the reflection at the metal covering layer and the scattering by the incorporated pigment particles. In order to increase the luster, the pigments can also be provided on both sides with a thin, semi-permeable metal layer, which is particularly preferred.

In another special embodiment of the pigments according to the invention, the matrix provided with pigment particles is provided with a thin, smooth metal oxide layer, the refractive index of the metal oxide layer being greater than the refractive index of the matrix material. Examples of suitable metal oxides are titanium dioxide, zirconium dioxide, zinc oxide, iron oxide and/or further highly refractive metal oxides. The metal oxide layer, the thickness of which is typically between 20 and 250 nm, acts as an interference or luster a film and additionally possibly as an absorbing film in the case where the metal oxide is colored. The interference or luster effect arises because some of the light is reflected at the interfaces of surrounding medium/metal oxide layer and metal oxide layer/matrix surface, as a result of which the reflected rays interfere with one another and at a suitable thickness of the metal oxide layers produce interference colors. This is, as in the case of the matrix particles covered with a metal layer, a multi-particle effect, since the light reflected by different, parallel-aligned particles contributes to the enhancement of the interference color. The non-reflected portion of the light reenters the matrix where some of it, as described, is transmitted and some of it is scattered. This gives a lustrous and high-covering pigment which has an interference color dependent on the viewing angle and the color, which is not dependent on the viewing angle, of the incorporated absorption pigment particles, it being possible for the latter to be modified by the absorption color of the metal oxide layer. In order to increase the effect, in this case too both sides of the pigment can be coated with a metal oxide layer, which is particularly preferred.

Pigments having such a "color flop", body color independent of the viewing angle and interference color dependent on the viewing angle, can be employed, for example, in printing technology for originals protected against photocopying.

If carbon black is incorporated into the matrix as the insoluble colorant, then the black background causes the matrix material coated with, for example, titanium dioxide to produce a pigment in which the body color is identical to the interference colour. In this way, a new type of pigment is obtained.

The coating of the platelet-shaped matrix particles which contain an insoluble and/or soluble colorant is carried out by known processes according to DE 2,009,566, DE 2,313,331, DE 3,151,355 or DE 3,221,045.

The coating of transparent matrix platelets with highly refractive metal oxides gives particularly transparent, high-luster pigments.

Apart from the two special embodiments described of the pigments according to the invention, the invention also comprises those having a more complicated structure. Thus, for achieving particular color effects or special functional properties, the pigments can be covered with one or more further metal oxide layers. By way of example, it may be mentioned that the pigments are provided with an additional tin dioxide or cerium dioxide covering layer, such as described in DE 35 35 818, in order to increase the stability in enamels and glazes. Furthermore, an additional metal oxide layer composed, for example, of tin oxide doped with antimony oxide (DE 38 42 330) or other electrically conducting covering layers can impart electric conductivity to the pigments according to the invention. A special optical effect can be achieved, for example, by combining an uncolored metal oxide layer with a colored metal oxide layer, as proposed, for example, in U.S. Pat. No. 3,087,828. Pigments according to the invention containing no more than 2 metal oxide layers are preferred.

For the protection of, for example, Al metal layers which are sensitive to hydrolysis, it is possible to apply, for example, polymer protective layers composed, for example, of polyethylene, polyacrylates or other materials. Furthermore, metal layers can also be combined with metal oxide layers for achieving special effects; thus, for example, a sequence of metal/metal oxide/metal layers on the matrix surface can act as a particularly effective interference layer, the thickness of the metal oxide layer determining the optical path difference between the rays reflected by the metal layers and thus the interference color.

The thickness of the covering layers can vary within a wide range. Thus, the thickness of semi-permeable metal layers is typically between 5 and 25 nm, while the thickness of metal oxide layers, as a rule, is between 20 and 300 nm. Polymer protective layers are, as a rule, not thicker than 50 nm. The ratio of the thickness of the matrix to the thickness of the layers applied on one side of the pigment according to the invention is between 0.01 and 500 and in particular between 0.1 and 150.

The covering power and, in the case of colored pigment particles, the absorption color of the pigments according to the invention, which is independent of the viewing angle, can be varied within a relatively wide range by the concentration of the incorporated pigment particles. The percentage by weight of the incorporated pigment particles, relative to the weight of the uncoated substrate, is typically between 0.5 and 40% and in particular between 5 and 25%. Particular preference is given to pigments according to the invention comprising white or black pigments, titanium dioxide or carbon black particles being used here in particular.

The color of pigments containing incorporated carbon black particles can range, for example, from off-white to light grey, metal-colored, dark grey and ultimately black, depending on the concentration of the carbon black particles of particular interest are metal-colored and in particular aluminium-colored pigments. Since these pigments are given luster by means of the subsequent coating using thin transparent metal oxide layers composed, for example, of titanium oxide, zirconium oxide, tin oxide or zinc oxide, they can replace platelet-shaped metal pigments, for example, in water paint formulations, where metal pigments and in particular aluminum pigments can only be used if provided with protective layers made, for example, of organic polymers, owing to the corrosion problems (evolution of hydrogen). Moreover, problems often arise even in corrosion-protected metal pigments, since the organic protective layer can be mechanically damaged ("scratched"). The metal-colored, lustrous pigments according to the invention which contain carbon black incorporated in a transparent matrix are chemically and mechanically extremely stable and have high brilliance and are aesthetically very attractive. They are therefore suitable in particular as substitutes for metallic pigments in a wide range of applications, in particular for formulations based on water.

Furthermore, preference is also given to pigments according to the invention containing one or more organic or inorganic and in particular inorganic pigments; carbon black, titanium dioxide, iron oxides, chromium oxides, cobalt oxide and colored spinels, such as, for example, cobalt aluminate, are used particularly preferably.

A particularly high luster is usually obtained when metal layers are used, but aesthetically impressive luster effects can also be achieved by means of metal oxide layers. Accordingly, the pigments according to the invention can be optimized in a wide range with respect to the particular application even with respect to the luster obtainable.

The aesthetic overall impression of the pigments according to the invention can, if desired, be emphasized and rounded off by an interference effect, as described above. Thus, the pigments according to the invention are optical systems having an excellent combination of optical properties, whose relative prominence can moreover be varied and optimized in a wide range with respect to the particular application. This optimization can be carried out routinely by one skilled in the art on the basis of the present description without the need for an inventive step.

The pigments according to the invention are prepared in a continuous process with the aid of a continuous belt, for example in a continuous belt process or in a continuous drum process.

First, the belt process will be illustrated by the schematic plan in FIG. 1. The continuous belt 1, which is guided by a roller system 2, runs through an application section, where it is coated with a thin film of the precursor. The application of the precursor together with the colorant is carried out by known processes, for example by means of a roll system 3 or a nozzle 4. This nozzle can be formed as a single-substance or multi-substance nozzle. Additionally, to adjust the layer thickness of the applied film a variable baffle 5 or an airbrush, in which a keen stream of air is blown through a slit nozzle, can be fitted. Coating of the belt by means of a doctor blade or dip-coating is also possible.

The combination of dip-coating one side or both sides of the belt with subsequent levelling of the applied layer with the aid of an airbrush has proven particularly advantageous.

The colorant is either dispersed or dissolved in the precursor before application to the belt, or the components are applied to the belt separately by means of a number of nozzles. The pigment particles are dispersed in the precursor by known methods, for example by an ultrasonic bath. Dispersion with the aid of a bead mill has proven particularly advantageous.

The coated belt is then passed through a drying section, which can consist of one or more sections. A preferred embodiment of the drying zone consists of a predrying device 6, in which the film is treated with hot air of temperature 80–150° C., and a following IR drying device 7. Apart from this, however, other embodiments of the drying zone are also possible. The total heating power of the drying zone is dependent, inter alia, on the running speed of the belt and is between 0.5 and 10 kW per m belt width. The running speed of the belt is between 1 and 1000 m/min and in particular between 100 and 500 m/min, though relatively large deviations from these values are also possible. The person skilled in the art can adjust the heating power of the drying zone and the running speed of the transport belt without any problem.

The use of sodium silicate as a precursor necessitates an acid bath 8, in which the alkali metal silicate film applied to the belt is reacted to give silicon dioxide. The alkali metal ions are then washed out of the matrix in the washing vessel 9.

Acid treatment is carried out either by passing the belt through a vessel filled with acid or by gassing the film applied with hydrogen chloride.

The concentration of the acid is adjusted to 1% to 20%, preferably to 5% to 15%. Acids which can be used are: hydrochloric acid, phosphoric acid, sulfuric acid, nitric acid, titanium tetrachloride solution, iron chloride solution, tin chloride solution and also organic acids, such as, for example, acetic acid.

The conditions in the acid bath must be chosen so that essentially only the alkali metal ions diffuse out, while the other cations added remain. Since alkali metal ions have very high diffusion coefficients for the diffusion out of the $SiO_2$ matrix taking place in the acids, a selective dissolving-out of the alkali metal ions can in general be effected by choosing a short residence time of the film in the acid bath or by using a weak acid such as, for example, phosphoric acid.

The layer formed is then removed from the belt by a device. Removal can either take place mechanically by scraping or brushing or without contact by dissolution of a "release layer" or by ultrasound. Removal with a liquid or gas stream 10 has proven advantageous. The separation of the film in the moist state is particularly sparing in terms of material, since the film then adheres poorly to the belt and the moist material scratches the belt less on separation.

If it is intended to coat the matrix platelets with metal oxide layers, a wet-chemical reaction layer is inserted after the belt process, in which the platelet-shaped matrix material is suspended in water and coated with a smooth metal oxide or metal hydroxide covering layer by addition of one or more metal salt solutions at a pH suitable for the deposition of the respective metal oxides or metal hydroxides. Mixed oxide or hydroxide layers and also several covering layers can also be deposited successively. This subsequent wet-chemical reaction step is known per se and described in DE 1,959,988, DE 2,215,191, DE 2,244,298, DE 2,313,331, DE 2,522,572, DE 3,137,808, DE 3,137,809, DE 3,151,343, DE 3,151,355, DE 3,211,602 and DE 3,235,017.

For better adhesion of the metal oxide layer to the matrix, it is expedient to coat the matrix first with a tin dioxide layer.

If it is intended to prepare pigments having a metal covering layer, the belt with the dried film is passed through a PVD zone.

Coating with metals, for example, with silver, copper or gold, can also be carried out, however, in a wet-chemical process.

To guarantee a continuous belt process, the belt is in this case preferably passed through vacuum chambers connected one after the other, which are evacuated to a different extent. Metal deposition then as a rule takes place by evaporation, sputtering or plasma polymerization in the innermost chamber, which has the best vacuum.

Continuous belt processes are known from U.S. Pat. No. 3,138,475 or EP 0,240,952.

Instead of the arrangement described, it is also possible to use other devices. Thus, for example, a quasi-continuous process can also be carried out by means of an arrangement analogous to the device shown in U.S. Pat. No. 3,767,443, FIG. II. In that arrangement, a very long support belt is wound on a drum (item 12 of FIG. II from U.S. Pat. No. 3,767,443); the belt is then unwound via a coating section in which first a release layer and then the sodium silicate film are applied, the latter being subsequently dried and, if desired, reacted with a mineral acid. The coated support belt is then wound onto X a storage drum (item 15 in FIG. II). After winding of the entire support belt is complete, the storage drum is placed in a bath in which the release layer is dissolved, as a result of which the dried matrix film is removed from the support belt. In general, the coated support film is not treated with a mineral acid before it is e wound onto the storage drum, since this results in separation of part of the $SiO_2$ film obtained from the support belt. After dissolution of the release layer matrix platelets are present which are removed and treated with a mineral acid.

The drum arrangement described can also be used for a quasi-continuous process. To this end, the support belt is coated in a first step with the precursor, which is then dried. After complete winding of the support belt coated with the dried matrix film onto the storage drum, the precursor container is exchanged for a mineral acid bath; the coated support belt is then unwound through the mineral bath, during which the direction of travel of the support belt changes and the supply and storage rollers are swapped over. After going through the acid bath and, if necessary, past a scraping device, the support belt has been freed of the matrix film, and a new cycle can start. This modified drum process is a variation of the continuous belt process shown in FIG. 1 and often has the advantage over the latter in that the corresponding arrangement can be built in a more compact manner; a disadvantage is that, after the belt has been completely unwound, the sodium silicate and acid containers need to be changed.

The arrangements described here are to be understood as examples and are intended to illustrate the invention without limiting it. In general, continuous processes are preferred over quasi-continuous or even batchwise processes.

It has been found that the use of belts based on thermally stable plastics is in many cases advantageous. The softening temperature of the plastic should preferably not be less than 150° C. and in particular not less than 180° C., in order to ensure sufficiently high drying temperatures. Furthermore, the plastic material should be chemically substantially inert and in particular should not be attacked by dilute mineral acids. Examples of suitable belt materials are polyethylene terephthalate, other polyesters and polyacrylates, this list only serving for illustration and not being intended to limit the invention.

The plastic belts typically have thicknesses of some 10 $\mu$m to a few mm, thicknesses of between 0.1 and 2 mm being particularly preferred. However, in extreme cases thicker plastic belts can also be used. The width and length of the plastic belts is in general less critical and can be optimized with respect to the particular requirements.

Plastic belts of this type usually have a smooth surface anyway.

However, it is also possible to use thin metal belts made of, for example, acid-resistant coated stainless steel or other metals inert to dilute mineral acids, the geometrical dimensions of these belts being substantially identical to those of plastic belts. The metal belts have high flexibility and stability and can be polished by conventional processes in order to increase the surface quality.

If desired, first a release layer can be applied to the belt used as support in order to facilitate the peeling-off of the matrix film; in quasi-continuous processes, it may be absolutely necessary to apply a release layer.

An example of a layer which can serve as release layer can be a thin layer of a water-soluble polymer, such as, for example, polyvinyl alcohol PVA, which dissolves in the acid bath and thus leads to complete removal of the matrix film. The materials proposed in U.S. Pat. No. 3,138,475 for the release layer are silicone varnishes and substances, such as, for example, hard waxes which evaporate or decompose upon heating without formation of soot. The use of a release layer even in continuous processes has the advantage that it may be possible to do without a scraping device.

The pigments according to the invention can also be prepared with the aid of a continuous drum process which will be explained below using the schematic plan in FIG. 2.

Arranged on a rotating drum (1) at specific intervals are the devices for the individual process steps, as have already been described for a continuous belt. A precursor is applied to the acid-resistant surface as a thin film. Application is preferably carried out by means of a roll system 2, but it can also be carried out by means of a spray device 3. The drum then passes through a zone which is designed as a drying zone or reaction zone. The liquid film is solidified here by either treating it with radiation by means of a device 4 and/or treating it with reagents, for example with acid, by means of a spray device 5.

The film can be solidified by infrared rays, by microwaves, by hot air or by heating of the drum from inside.

The layer obtained is removed from the drum surface by a separation device 6. The removal can be carried out with the aid of an air nozzle, a so-called air knife, by a water jet or by a mechanical device. The platelet-shaped material obtained is then further processed, as already described.

The precursor used for the preparation of the pigments according to the invention is preferably commercially available sodium silicate; thus, a 35% sodium silicate, this being the percentage by weight relative to the weight of sodium silicate, is available from E. Merck, Darmstadt under the name sodium silicate, very pure (Order No. 5621).

In addition the silicates or mixtures thereof may be employed as precursor solutions of inorganic or organic compounds of the metals aluminum, silicon, potassium or sodium with borates, chlorides, aluminates or poly- or meta-phosphates. Potassium silicate or ammonium silicate or their mixtures can also be used. Depending on its concentration, the commercially available sodium silicate is preferably diluted with water until an approximately 5–25%, and in particular 10–20%, aqueous solution is present.

The properties of the sodium silicate solution and the matrix can be modified by means of additives. Thus, for example, an addition of sodium aluminate solution (Si: Al ratio approximately 100:1) causes a change in the properties of the matrix particles which can lead to a better processability. Particularly preferred additives are aluminate, borate and/or phosphate.

In addition, other additives, for example surface-active substances or viscosity improvers, can also be added to the sodium silicate solution.

At a constant belt speed, the thickness of the sodium silicate film applied to the support belt is optionally controlled by the variable baffle. The belt is held very flat in the baffle region by suitably arranged rollers, i.e. any "sagging" is avoided. At the bottom, the baffle is preferably knife-shaped; the baffle edge is very precisely adjusted, the distance between the lower edge of the baffle and the belt surface typically being between about 1 and 20 $\mu$m. The distance can typically be adjusted to an accuracy of about ±1 $\mu$m or less. Since at a sodium silicate concentration of about 15% the thickness of the $SiO_2$ particles obtained after igniting has been decreased to about 1/10 the thickness of the original sodium silicate film, this means that the layer thickness tolerance of the $SiO_2$ particles is about ±0.1 $\mu$m; the layer thickness of the $SiO_2$ particles is 0.5 $\mu$m or more, if this is 20% or less, which in general can be considered as adequate. With very common layer thicknesses in practice of about 1 $\mu$m or more, the layer thickness tolerance is 10% or less. If it is intended to obtain very thin platelets having a thickness of, for example, less than 0.5 $\mu$m having a layer thickness tolerance of about 10%, more strongly diluted sodium silicate solutions can be used for this purpose.

By the choice of the concentration of the sodium silicate solution and the drying conditions, the layer thickness and the layer thickness tolerance of the substrates according to the invention can be influenced in a controlled manner and very thin particles having a layer thickness tolerance (=standard deviation of the layer thickness) of about 10% can also be obtained. Platelet-shaped silicon substrates having a well-defined layer thickness distribution of this type are not described in the prior art and are also not available using the known preparation processes.

The platelet-shaped pigments prepared by the process according to the invention are distinguished by an excellent surface quality and a very uniform thickness. The standard deviation, called thickness tolerance, is not greater than 10%. As a result of the plane-parallel surface and the narrow thickness tolerance of the matrix platelets, a very high color purity and very high color strength are achieved. With respect to their properties, for example their covering power, they can be made to measure with respect to the particular application, since the covering power depends on the number of pigment particles in the matrix. The more pigment particles are suspended in the matrix, the larger the covering power.

The color of pigments which contain incorporated carbon black particles can range, depending on the concentration of the carbon black particles, for example, from off-white via light grey, metal-colored, dark grey to black. Metal-colored and in particular aluminum-colored pigments are of particular interest.

The pigments prepared by the process according to the invention have a very wide range of application.

They can be used in formulations such as paints, cosmetics or plastics. The pigments can have a high aspect ratio. They can therefore be added to paints or plastics as diffusion barriers, for example especially as anticorrosion agents (diffusion barriers for oxygen).

The entire disclosures of all applications, patents and publications, cited above and below, and of corresponding applications DE P 4134600 (10.18.1991), DE P 4138376 (11.22.1991), DE P 4212119 (04.10.1992), DE P 4215276 (05.09.1992) are included in this application by way of reference.

The examples given below are intended to illustrate the invention without limiting it.

EXAMPLE 1

Figure 1:
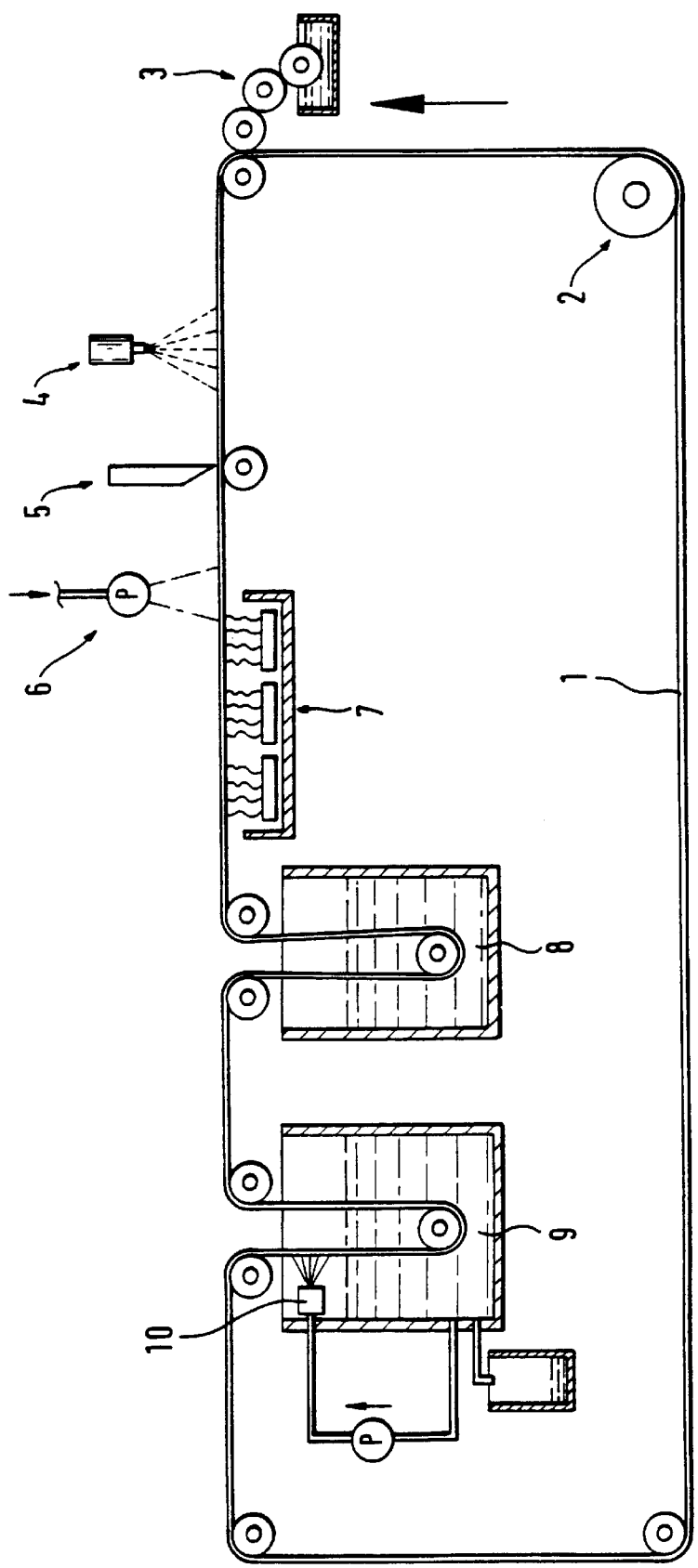
FIG. 1 is a schematic of a continuous belt process.
Figure 2:
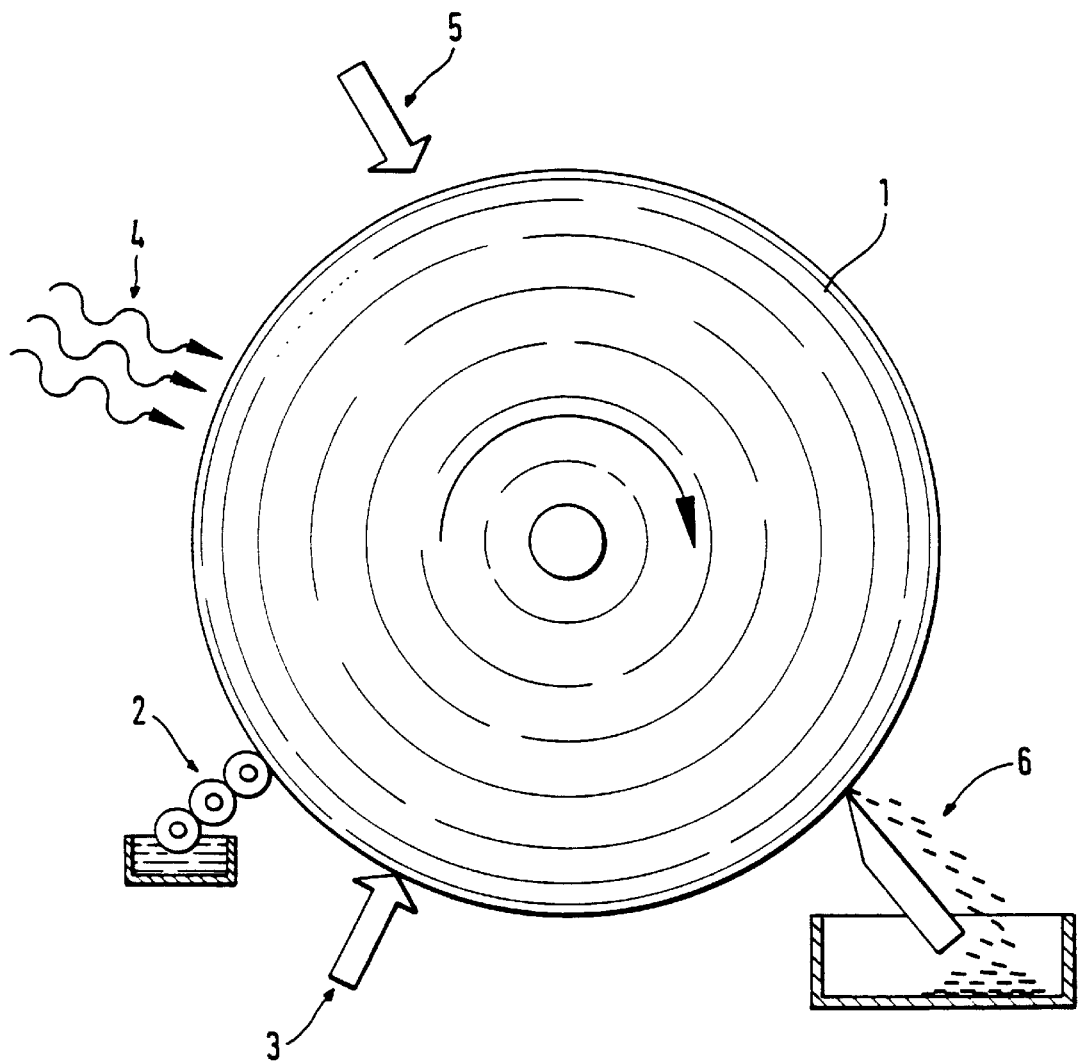
FIG. 2 is a schematic of a continuous drum process.

A revolving belt of polyethylene terephthalate (Melinex O; manufacturer ICI; width: 12.5 cm; speed: 10 m/min) is coated with a sodium silicate film of about 10 $\mu$m thickness by reverse roll coating. The sodium silicate solution is prepared by dilution of commercially available sodium silicate (very pure sodium silicate, manufacturer: E. Merck) with water in the ratio 1 to 2.5, 0.2% by weight of a surfactant (Pricol extra, manufacturer: Henkel) also being admixed. The diluted sodium silicate solution has a silicon dioxide content of 7.7%. The sodium silicate film is dried in a drying section by treatment with infrared radiation and hot air. The belt then passes through an acid bath containing 10% hydrochloric acid and subsequently a water bath. On leaving the water bath, the gel-like silicon dioxide film is peeled off by means of a water jet and rinsed in the water bath. The platelet-shaped fragments are filtered in a filter centrifuge and washed with completely demineralized water until a pH of 5 to 6 is established. The filter cake is comminuted in a laboratory mill (Rotor GT 800, manufacturer: Rotor) in aqueous suspension in stage 5.

The $SiO_2$ platelets obtained have a diameter of 20 to 100 μm and an average thickness of 500 nm.

EXAMPLE 2

6 g of wetting auxiliary (Pricol GV; manufacturer: Henkel) are dissolved in 2 l of completely demineralized water. 1 l of very pure sodium silicate (manufacturer: E. Merck) is stirred into this solution. 100 ml of an aluminate stock solution which is prepared by dissolving 32 g of sodium aluminate in 500 ml of completely demineralised water are added to this solution.

The solution is processed, as described in Example 1, on a continuous belt.

A platelet-shaped $SiO_2$ matrix containing aluminum as the network-forming agent in a concentration of 1 atom % relative to silicon is obtained.

EXAMPLE 3

6 g of wetting auxiliary (Pricol GV; manufacturer: Henkel) are dissolved in 2 l of completely demineralized water. 1 l of very pure sodium silicate (manufacturer: E. Merck) is stirred into this solution. 100 ml of a borate stock solution which is prepared by dissolving 21 g of boric acid (manufacturer: E. Merck) in 300 ml of completely demineralised water and adjusting the pH to a value of 12 with dilute sodium hydroxide solution are added to this solution.

The solution is processed, as described in Example 1, on a continuous belt.

A platelet-shaped $SiO_2$ matrix containing boron as the network-forming agent in a concentration of 1 atom % relative to silicon is obtained.

EXAMPLE 4

6 g of wetting auxiliary (Pricol GV; manufacturer: Henkel) are dissolved in 2 l of completely demineralized water. 1 l of very pure sodium silicate (manufacturer: E. Merck) is stirred into this solution. 100 ml of a phosphate stock solution which is prepared by dissolving 24 g of $Na_2HPO_4 \times 12\ H_2O$ (manufacturer: E. Merck) in 300 ml of completely demineralized water and adjusting the pH to a value of 12 with dilute sodium hydroxide solution are added to this solution.

The solution is processed, as described in Example 1, on a continuous belt.

A platelet-shaped $SiO_2$ matrix containing phosphorus as the network-forming agent in a concentration of 1 atom % relative to silicon is obtained.

EXAMPLE 5

100 g of $SiO_2$ platelets are suspended in 1500 ml of completely demineralized water. First, an $SnCl_4$ solution (preparation: 11.5 g of $SnCl_4$ are mixed with 38 ml of concentrated hydrochloric acid and this solution is made up to 192 ml with completely demineralized water) is added dropwise with vigorous stirring at 75° C. and pH 1.8 at a dose rate of 0.5 ml/min. A $TiCl_4$ solution ($TiCl_4$ content: 375 g/l) is then added dropwise under identical conditions and at an identical dose rate. The pH is in each case kept constant by addition of 16% sodium hydroxide solution.

After about 110 ml have been added, the product is filtered, washed with completely demineralised water until neutral, dried and ignited at 800° C. for 30 min.

A highly transparent, silver-colored interference pigment having excellent luster is obtained.

The colouristic data compared with a silver-coloured interference pigment based on mica (Iriodin 130, manufacturer: E. Merck) are contained in Table 1.

EXAMPLE 6

100 g of $SiO_2$ platelets are suspended in 1500 ml of completely demineralized water. First, an $SnCl_4$ solution (preparation: 11.5 g of $SnCl_4$ are mixed with 38 ml of concentrated hydrochloric acid and this solution is made up to 192 ml with completely demineralized water) is added dropwise with vigorous stirring at 75° C. and pH 1.8 at a dose rate of 0.5 ml/min. A $TiCl_4$ solution (TiCl, content: 375 g/l) is then added dropwise under identical conditions and at an identical dose rate. The pH is in each case kept constant by addition of 16% sodium hydroxide solution.

After about 220 ml have been added, the product is filtered, washed with completely demineralized water until neutral, dried and ignited at 800° C. for 30 min.

A highly transparent, golden yellow-colored interference pigment having excellent luster is obtained.

The coloristic data compared with a golden yellow-colored interference pigment based on mica (Iriodin 207, manufacturer: E. Merck) are contained in Table 1.

EXAMPLE 7

100 g of $SiO_2$ platelets are suspended in 1500 ml of completely demineralized water. First, an $SnCl_4$, solution (preparation: 11.5 g of $SnCl_4$ are mixed with 38 ml of concentrated hydrochloric acid and this solution is made up to 192 ml with completely demineralized water) is added dropwise with vigorous stirring at 75° C. and pH 1.8 at a dose rate of 0.5 ml/min. A $TiCl_4$ solution ($TiCl_4$ content: 375 g/l) is then added dropwise under identical conditions and at an identical dose rate. The pH is in each case kept constant by addition of 16% sodium hydroxide solution. If necessary, products formed by secondary hydrolysis must be removed by sedimentation.

After about 570 ml have been added, the product is filtered, washed with completely demineralized water until neutral, dried and ignited at 800°C. for 30 min.

A highly transparent, red-colored interference pigment having excellent luster is obtained.

The coloristic data compared with a red-coloured interference pigment based on mica (Iriodin 215, manufacturer: E. Merck) are contained in Table 1.

EXAMPLE 8

100 g of $SiO_2$ platelets are suspended in 1500 ml of completely demineralized water. An $FeCl_3$ solution ($FeCl_3$ content: 5.4%) is added dropwise with vigorous stirring at 75° C. and pH 4.0 at a rate of 0.5 ml/min. The pH is kept constant by addition of dilute sodium hydroxide solution.

After about 1200 ml have been added, the product is filtered, washed with completely demineralized water until neutral, dried and ignited at 800° C. for 30 min.

A luminous bronze-colored effect pigment having excellent luster and high brilliance is obtained.

The colouristic data compared with a bronze-colored effect pigment based on mica (Iriodin 530, manufacturer: E. Merck) are contained in Table 1.

Example 9

100 g of $SiO_2$ platelets are suspended in 1500 ml of completely demineralized water. An iron chloride solution ($FeCl_3$ content: 5.4%) is added dropwise with vigorous stirring at 75° C. and pH 4.0 at a rate of 0.5 ml/min. The pH is kept constant by addition of dilute sodium hydroxide solution. If necessary, products formed by secondary hydrolysis must be removed by sedimentation.

After about 1375 ml have been added, the product is filtered, washed with completely demineralized water until neutral, dried and ignited at 800° C. for 30 min.

A highly transparent, red-colored effect pigment having excellent luster is obtained.

The coloristic data compared with a wine-red-colored effect pigment based on mica (Iriodin 534, manufacturer: E. Merck) are contained in Table 1.

EXAMPLE 10

Apart from 0.2% by weight of a surfactant (Pricol extra, manufacturer: Henkel) additionally 0.2% by weight of Methylene Blue (manufacturer: E. Merck) are added to the sodium silicate solution described in Example 1. The mixture is applied to a continuous belt as described in Example 1 and processed. The product obtained after grinding in the laboratory mill is dried for 60 minutes at 110° C.

Blue, lustrous $SiO_2$ platelets of high transparency are obtained.

EXAMPLE 11

200 g of the blue $SiO_2$ platelets obtained as in Example 7 are suspended in 2 l of completely demineralized water, and the suspension is heated to 60° C. and adjusted to pH 9 with 2 N sodium hydroxide solution. 250 ml of sodium silicate solution are metered in at a rate of 1 ml/min while stirring vigorously and keeping the temperature constant. The sodium silicate solution is prepared by diluting 26 ml of very pure sodium silicate (manufacturer: E. Merck) with 224 ml of completely All demineralised water. The pH is kept at 9 by controlled addition of dilute hydrochloric acid.

After coating with $SiO_2$, the product is directly additionally coated with a reflective metal oxide interference layer according to known processes, for example according to the process described in U.S. Pat. No. 4,086,100, Example 1.

EXAMPLE 12

An aqueous solution of citric acid (manufacturer: E. Merck) and $CrCl_3 \times 6B_2O$ (manufacturer: E. Merck) is added to the sodium silicate solution described in Example 1 in order to obtain a concentration of 7% citric acid and 3% $CrCl_3 \times 6H_2O$ in the sodium silicate solution. 3% Texapon® (manufacturer: Henkel) are additionally added as the wetting auxiliary. The mixture is applied to a continuous belt as described in Example 1 and processed. The product obtained after grinding in the laboratory mill is dried for 60 min at 110° C. Lustrous, olive-green platelets of high transparency are obtained.

EXAMPLE 13

An aqueous solution of sodium methylenediaminetetraacetate (manufacturer: E. Merck) and $CoCl_2 \times 6H_2O$ (manufacturer: E. Merck) is added to the sodium silicate solution described in Example 1 in order to obtain a concentration of 8% sodium methylenediaminetetraacetate and 3% $CoCl_2 \times 6H_2O$ in the sodium silicate solution. 3% Texapone® (manufacturer: Henkel) are additionally added as the wetting auxiliary. The mixture is applied to a continuous belt as described in Example 1 and processed. The product obtained after grinding in the laboratory mill is dried for 60 min at 110° C. Lustrous, lilac-colored platelets of high transparency are obtained.

EXAMPLE 14

An aqueous solution of tartaric acid (manufacturer: E. Merck) and $FeCl_3 \times 6H_2O$ (manufacturer: E. Merck) is added to the sodium silicate solution described in Example 1 in order to obtain a concentration 9 of 6% tartaric acid and 8% $FeCl_3 \times 6H_2O$ in the sodium silicate solution. 3% Texapone (manufacturer: Henkel) are additionally added as the wetting auxiliary. The mixture is applied to a continuous belt as described in Example 1 and processed. The product obtained after grinding in the laboratory mill is dried for 60 min at 110° C. Lustrous, brownish yellow-colored platelets of high transparency are obtained.

EXAMPLE 15

In a bead mill (Dispermat CV; manufacturer: VMA-Getzmann) 500 ml of a 3% dispersion of titanium dioxide particles (R506; manufacturer: Sachtleben Chemie; average particle size: 440 nm) in a sodium silicate solution (very pure sodium silicate; manufacturer: E. Merck; dilution ratio with water 1:2.5) are prepared. For better dispersibility 0.5% by weight, relative to titanium dioxide, of a stabiliser (HYDROPALAT® 884, manufacturer: Henkel) and for better wettability of the continuous belt 1% by weight, relative to the finished dispersion, of a wetting auxiliarly (HYDROPALAT® 875, manufacturer: Henkel) are added.

The dispersion was applied to a continuous belt as a thin film as described in Example 1 and the belt passed through a drying section where the film is dried by infrared rays and hot air. The belt is then passed through an acid bath and a water bath. On leaving the water bath, the gel-like film is separated from the belt by means of a water jet and rinsed in the water bath. The separated fragments of the film are processed as in Example 1.

100 g of the platelets obtained from the laboratory mill are suspended in 2.5 l of completely demineralized water and coated with titanium dioxide in the rutile form according to the process described in U.S. Pat. No. 4,086,100, Example 1.

A highly covering, white pigment having a silver luster is obtained.

EXAMPLE 16

12.3 g of DPP-Red (manufacturer: Ciba Geigy), particle size: 50 nm
1.2 g of stabiliser W-22 (manufacturer: Krahn-Chemie),
50 g of completely demineralized water and
200 g of zirconium beads (1–2.5 mm)
are ground for 90 min at 2000 rpm. The beads are then sieved and the suspension obtained is stirred with 800 ml of completely demineralized water and 300 ml of very pure sodium silicate (manufacturer: E. Merck). The mixture is processed on a continuous belt as described in Example 1. The platelets obtained from the laboratory mill are dried at 110° C. for one hour. A lustrous red pigment is obtained.

EXAMPLE 17

50 g of the platelets obtained in Example 16 are suspended in 1 l of water. First, an SnCl$_4$ solution (preparation: 5.8 g of SnCl$_4$5 H$_2$O dissolved in 7 ml of concentrated hydrochloric acid and 75 ml of water) is metered in while stirring vigorously at 75° C. and pH 1.8 at a rate of 0.6 ml/min. The temperature is then in-creased to 90° C. and the pH reduced to 1.5. During the addition of TiCl$_4$ solution (TiCl$_4$ content=380 g/l) at 0. 6 ml/min, the pH is in each case kept constant by addition of dilute sodium hydroxide solution.

After addition of about 100 ml of TiCl$_4$ solution, a silver-colored interference, after 195 ml a red interference, after 275 ml a blue interference and after 300 ml a green interference is obtained.

The products are filtered, washed and dried. The different interference color pigments show, independently of the viewing angle, the red body color of the substrate and, depending on the viewing angle, the interference color due to the TiO$_2$ coating, i.e. a color flop effect.

Coloristic Measurements for the color flop pigment

The measurements given are CIE-L*A*B* values of a 1.7% paint chart on a black background. The measuring geometry was: the interference color 70° (illumination)/95° (measurement) [luster], the body color 450 (illumination)/90° (measurement).

| Interference colour | | A* | B* | | A* | B* |
|---|---|---|---|---|---|---|
| silver | 70*/95* lustre | 2.8 silver | 1.9 | 45*/90* according to body colour | 14.7 | 0.8 red |
| red | 70*/95* lustre | 25.3 red | 6.4 | 45*/90* according to body colour | 21.2 | 8.1 red |
| blue | 70*/95* lustre | −12.7 blue | −11.5 | 45*/90* according to body colour | 6.4 | −3.3 red |
| green | 70*/95* lustre | −13.0 green | 13.9 | 45*/90* according to body colour | 6.4 | 3.1 red |

Figure 3:
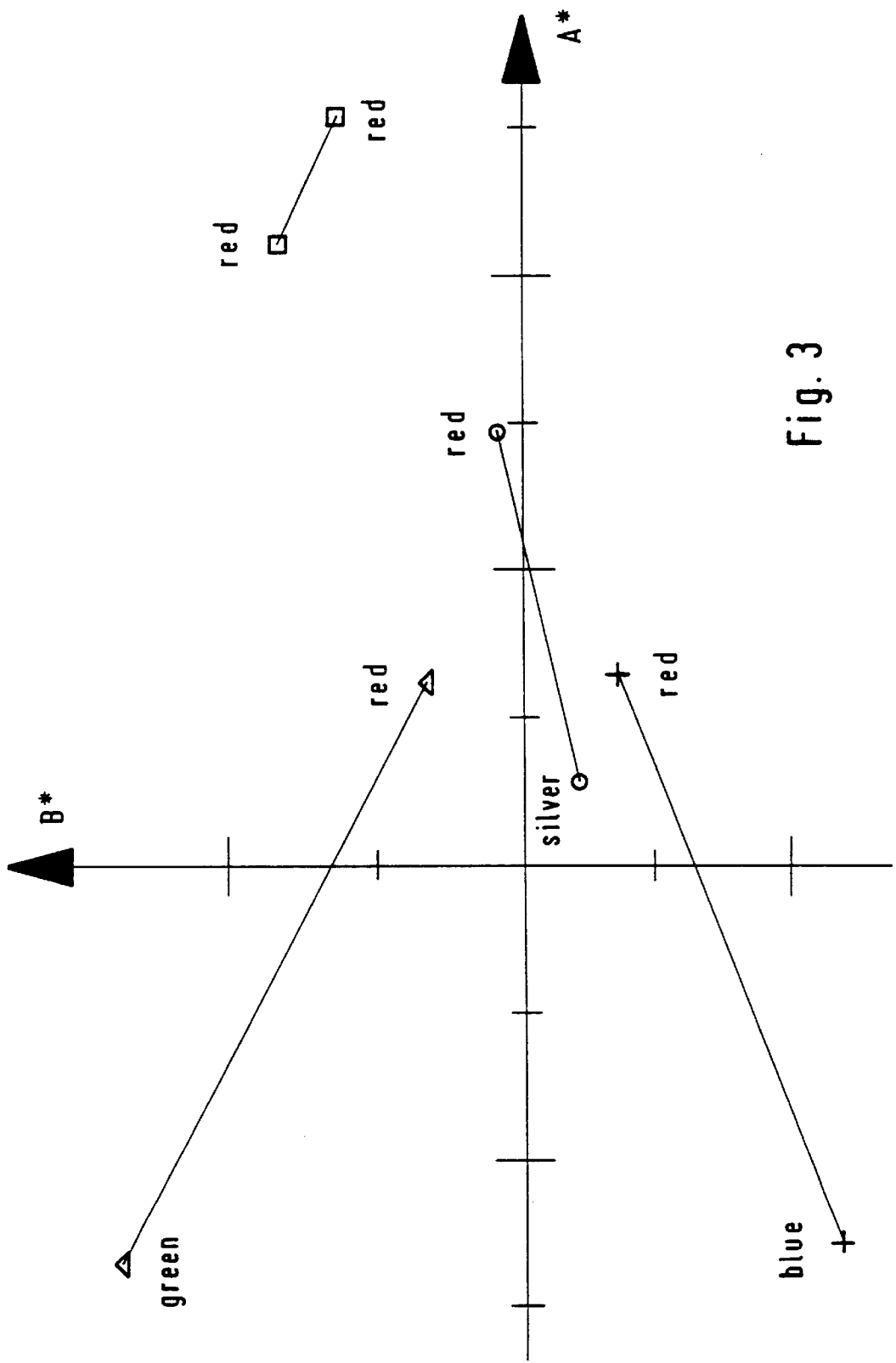
FIG. 3 is a graph of coloristic measurements for the color flop pigment of Example 17.

The color locations [sic] obtained are shown in FIG. 3.

EXAMPLE 18

82.2 g of DERUSSOL C (carbon black dispersion w=21%, manufacturer: Degussa) are stirred with 300 ml of very pure sodium silicate (manufacturer: E. Merck) and 680 ml of completely demineralized water. 2.1 g of Pricol (manufacturer: Henkel) are then dissolved in the suspension as a wetting auxiliary. The suspension is processed on a continuous belt as described in Example 1. The platelets obtained from the laboratory mill are suspended in water and coated with titanium dioxide according to the process described in U.S. Pat. No. 4,086,100.

The coated platelets are ignited at 800° C. under protective gas and worked up in a known manner. Depending on the thickness of the TiO$_2$ interference layer, variously colored (for example silver, gold, red, blue, green) body color pigments are obtained.

EXAMPLE 19

115.3 g of iron oxide red (manufacturer: BAYER),
3.9 g of stabiliser W-22 (manufacturer: Krahn-Chemie),
600 g of completely demineralized water and
200 g of zirconium beads (diameter: 1–2.5 mm)
are ground in a bead mill for 1 hour at 3000 rpm. After sieving the beads, the suspension is stirred with 2250 ml of completely demineralised water and 1140 ml of very pure sodium silicate (manufacturer: E. Merck).

The suspension is processed on a continuous belt as described in Example 1. The red platelets obtained from the laboratory mill are suspended in water and coated in interference colors with metal oxides according to known processes, for example according to the process described in U.S. Pat. No. 4,086,100.

EXAMPLE 20

115.3 g of iron oxide yellow (manufacturer: BAYER),
3.9 g of stabiliser W-22 (manufacturer: Krahn-Chemie),
600 g of completely demineralized water and
200 g of zirconium beads (diameter: 1–2.5 mm)
are ground in a bead mill for 1 hour at 3000 rpm. After sieving the beads, the suspension is mixed with 2250 ml of completely demineralized water and 1140 ml of sodium silicate (manufacturer: E. Merck).

The suspension is processed on a continuous belt as described in Example 1. The yellow platelets obtained from the laboratory mill are suspended in water and coated in interference colors with metal oxides according to known processes, for example according to the process described in U.S. Pat. No. 4,086,100.

EXAMPLE 21

115.3 g of iron oxide black (manufacturer: CRODA),
3.9 g of stabiliser W-22 (manufacturer: Krahn-Chemie),
600 g of completely demineralised water and
200 g of zirconium beads (diameter: 1–2.5 mm)
are ground in a bead mill for 1 hour at 3000 rpm. After sieving the beads, the suspension is mixed with 2250 ml of completely demineralised water and 1140 ml of very pure sodium silicate (manufacturer: E. Merck).

The suspension is processed on a continuous belt as described in Example 1. The black platelets obtained from the laboratory mill are suspended in water and coated in interference colors with metal oxides according to known processes, for example according to the process described in U.S. Pat. No. 4,086,100.

EXAMPLE 22

115.3 g of chromium oxide (manufacturer: CRODA),
3.9 g of stabiliser W-22 manufacturer: Krahn-Chemie),
600 g of completely demineralized water and
200 g of zirconium beads (diameter: 1–2.5 mm)
are ground in a bead mill for 1 hour at 3000 rpm. After sieving the beads, the suspension is mixed with 2250 ml of completely demineralised water and 1140 ml of very pure sodium silicate (manufacturer: E. Merck).

The suspension is processed on a continuous belt as described in Example 1. The green platelets obtained from the laboratory mill are suspended in water and coated in interference colors with metal oxides according to known processes, for example according to the process described in U.S. Pat. No. 4,086,100.

EXAMPLE 23

115.3 g of Berlin Blue (manufacturer: CRODA),
3.9 g of stabiliser W-22 (manufacturer: Krahn-Chemie),
600 g of completely demineralized water and
200 g of zirconium beads (diameter: 1–2.5 mm)
are ground in a bead mill for 1 hour at 3000 rpm. After sieving the beads, the suspension is mixed with 2250 ml of completely demineralized water and 1140 ml of sodium silicate (manufacturer: E. Merck).

The suspension is processed on a continuous belt as described in Example 1. The blue platelets obtained from the laboratory mill are suspended in water and coated in interference colors with metal oxides according to known processes, for example according to the process described in U.S. Pat. No. 4,086,100.

EXAMPLE 24

100 g of the $SiO_2$ platelets obtained as in Example 1 are dispersed in a mixture of
1000 ml of a 3% silver nitrate solution,
25 ml of a 40% formalin solution and
25 ml of methanol.

The suspension is stirred slowly overnight until all the silver from the solution has been deposited onto the $SiO_2$ platelets.

The silver-grey platelets obtained are washed, dried and ignited at 800° C.

A silver-grey pigment is obtained.

TABLE 1

| | 45°/0° b.b. | | | lustre ⟨ b.b. | | | 45°/0° w.b. | | | | |
|---|---|---|---|---|---|---|---|---|---|---|---|
| | L* | a* | b* | L* | a* | b* | L* | a* | b* | rel. lustre | covering power |
| TiO$_2$-coated Silver Types (Example 5) | | | | | | | | | | | |
| SiO$_2$-Silver | 32.9 | −1.6 | −7.9 | 83.2 | +2.6 | −8.3 | 80.2 | −1.6 | +5.3 | 60.5 | 21.1 |
| Iriodin 130 | 39.9 | −2.5 | −6.4 | 82.1 | +1.2 | −5.4 | 80.4 | −0.4 | +5.6 | 51.4 | 24.7 |
| Interference Types (Example 6) | | | | | | | | | | | |
| SiO$_2$-Yellowish Gold | 32.5 | −2.9 | +6.5 | 81.2 | −1.3 | +24.7 | 81.7 | +2.1 | −9.7 | 60.0 | 20.3 |
| Iriodin 207 | 46.5 | −2.5 | +6.2 | 77.6 | −0.4 | +20.9 | 83.8 | −0.5 | −3.0 | 40.1 | 26.8 |
| (Example 7) | | | | | | | | | | | |
| SiO$_2$-Red | 32.3 | +5.5 | −3.5 | 71.3 | +31.2 | −3.4 | 86.5 | −11.4 | +2.7 | 54.7 | 18.5 |
| Iriodin 215 | 32.4 | +10.2 | −2.8 | 62.6 | +27.6 | −2.5 | 88.3 | −7.4 | +4.2 | 48.2 | 17.9 |
| Fe$_2$O$_3$-Coated Types (Example 8) | | | | | | | | | | | |
| SiO$_2$-Bronze | 20.7 | +13.6 | +26.7 | 65.9 | +24.3 | +37.9 | 38.9 | +23.3 | +43.7 | 68.6 | 54.9 |
| Iriodin 530 | 37.3 | +11.9 | +24.7 | 80.8 | +13.2 | +27.9 | 44.9 | +23.8 | +32.4 | 53.8 | 131.6 |
| (Example 9) | | | | | | | | | | | |
| SiO$_2$-Wine Red | 14.4 | +19.5 | +13.7 | 51.9 | +36.3 | +4.8 | 38.2 | +34.8 | +41.9 | 72.3 | 42.90 |
| Iriodin 534 | 23.9 | −21.9 | +16.5 | 58.9 | +33.8 | +9.0 | 44.5 | +32.4 | +29.6 | 59.4 | 48.5 | b.b. = black background
w.b. = white background
lustre < = lustre angle

What is claimed is:

1. A platelet-shaped pigment, consisting essentially of an inorganic, platelet-shaped matrix containing silicon dioxide, a silicate, boron oxide, a borate, an aluminate or a mixture thereof, and optionally containing carbon black, coated with one or more thin, transparent or semi-transparent reflective layers of metal oxides selected from titanium dioxide, zirconium dioxide, zinc oxide, iron (III) oxide, chromium oxide or mixtures thereof which give the pigment an interference color effect, prepared by:

applying a liquid precursor of the matrix to a continuous belt as a thin film,
solidifying the liquid film by drying,
separating the resulting layer from the belt as particles and treating them with a mineral acid and washing them,
suspending the particles in water and
coating them with one or more reflective layers of the metal oxides.

2. The pigment of claim 1, wherein the particles are dried, calcined, ground and classified before suspending them in water and coating them with one or more reflective layers of metal oxides.

3. The pigment of claim 1, comprising a reflective layer consisting of chromium oxide, titanium dioxide, iron (III) oxide or a mixture thereof, giving the pigment an interference color effect.

4. A process for preparing a platelet-shaped pigment of claim 1 having high luster and high covering power or high transparency, said process comprising:

applying a liquid precursor of the matrix to a continuous belt as a thin film,
solidifying the liquid film by drying,
separating the resulting layer from the belt as particles and treating them with a mineral acid and washing them,
suspending the particles in water and
coating them with one or more reflective layers of metal oxides.

5. The process of claim 4, wherein the liquid precursor comprises a silicate, a borate, a chloride, an aluminate or a poly- or metaphosphate of a metal selected from silicon, potassium or sodium, or a mixture thereof.

6. The process of claim 5, wherein the liquid precursor comprises sodium silicate.

7. The process of claim 4, wherein the particles are dried, calcined, ground and classified before suspending them in water and coating them with one or more reflective layers of metal oxides.

8. A paint, printing ink, cosmetic, plastic or anti-corrosion formulation comprising a pigment according to claim 1.

9. The pigment of claim 1, wherein the liquid precursor comprises sodium silicate, potassium silicate, ammonium silicate or mixtures thereof.

10. The pigment of claim 1, having pigment particles with a layer thickness tolerance of about 10% or less.

11. The pigment of claim 1, consisting essentially of a silicon dioxide matrix coated with a metal oxide layer of titanium dioxide.

12. The pigment of claim 1, consisting essentially of a silicon dioxide matrix coated with a metal oxide layer of iron (III) oxide.

13. A platelet-shaped pigment, consisting essentially of an inorganic, platelet-shaped matrix containing silicon dioxide, a silicate, boron oxide, a borate, an aluminum oxide, an aluminate or a mixture thereof, and optionally containing carbon black, coated with a first thin, transparent layer of tin dioxide and a second thin, transparent layer of titanium dioxide, which give the pigment an interference color effect, prepared by:

applying a liquid precursor of the matrix to a continuous belt as a thin film, solidifying the liquid film by drying, separating the resulting layer from the belt as particles and treating them with a mineral acid and washing them, suspending the particles in water and coating them with the layers of tin dioxide and titanium dioxide.

14. The pigment of claim 9, wherein the liquid precursor further comprises carbon black.

15. The process of claim 5, wherein the liquid precursor further comprises carbon black.

16. The pigment of claim 1, wherein the inorganic, platelet-shaped matrix contains carbon black.

17. The pigment of claim 13, wherein the inorganic, platelet-shaped matrix contains carbon black.

* * * * *